(12) United States Patent
Dehaudt

(10) Patent No.: US 12,075,899 B2
(45) Date of Patent: Sep. 3, 2024

(54) DEVICE FOR PREPARING A COSMETIC COMPOSITION AND ASSOCIATED PROCESS

(71) Applicant: L'OREAL, Paris (FR)

(72) Inventor: Eric Dehaudt, Clichy (FR)

(73) Assignee: L'OREAL, Paris (FR)

(*) Notice: Subject to any disclaimer, the term of this patent is extended or adjusted under 35 U.S.C. 154(b) by 960 days.

(21) Appl. No.: 17/054,803

(22) PCT Filed: May 23, 2019

(86) PCT No.: PCT/EP2019/063306
§ 371 (c)(1),
(2) Date: Nov. 12, 2020

(87) PCT Pub. No.: WO2019/224294
PCT Pub. Date: Nov. 28, 2019

(65) Prior Publication Data
US 2021/0227950 A1    Jul. 29, 2021

(30) Foreign Application Priority Data
May 23, 2018  (FR) ..................... 18 54311

(51) Int. Cl.
*B65B 3/04*    (2006.01)
*A45D 34/04*   (2006.01)
(Continued)

(52) U.S. Cl.
CPC ............... *A45D 34/04* (2013.01); *A61K 8/11* (2013.01); *A61Q 19/00* (2013.01); *B65B 3/022* (2013.01);
(Continued)

(58) Field of Classification Search
CPC .. B65B 3/04; B65B 3/022; A61K 8/11; B65D 81/325
See application file for complete search history.

(56) References Cited

U.S. PATENT DOCUMENTS 2,591,706 A * 4/1952 Lockhart ............. A61M 5/2448
                                                 604/90
3,028,052 A * 4/1962 Archer ................ B01F 35/7137
                                                 222/386
(Continued)

FOREIGN PATENT DOCUMENTS

FR        3 007 014 A1    12/2014
WO    WO 2013/171621 A    11/2013

*Primary Examiner* — Gloria R Weeks
(74) *Attorney, Agent, or Firm* — POLSINELLI PC

(57) ABSTRACT

The invention relates to a device (10) for preparing a cosmetic composition comprising: —a structure defining a housing receiving at least one capsule (16) containing at least one constituent of the cosmetic composition, —an outlet nozzle (32), —a piston movable in translation in relation to the structure in the housing, suitable for perforating the or each capsule (16) and conveying contents of each capsule (16) to the outlet nozzle (32), and—a preform (54) fluidically connected to the outlet nozzle (32). The preform (54) has an inner surface (72) having a concavity lower than half of a thickness of the preform (54), intended to be arranged facing the housing and to be deformed by the conveyance of the contents of each capsule (16), so as to form a receptacle.

18 Claims, 5 Drawing Sheets

(51) Int. Cl.
*A61K 8/11* (2006.01)
*A61Q 19/00* (2006.01)
*B65B 3/02* (2006.01)
*A45D 34/00* (2006.01)

(52) U.S. Cl.
CPC .. *A45D 2034/005* (2013.01); *A45D 2200/055* (2013.01); *A45D 2200/058* (2013.01)

(56) References Cited

U.S. PATENT DOCUMENTS

| | | | | |
|---|---|---|---|---|
| 3,419,644 A * | 12/1968 | Edman | ................ | C06B 21/0058 425/130 |
| 3,514,919 A * | 6/1970 | Ashton | ................ | B65B 55/12 53/469 |
| 3,636,950 A * | 1/1972 | Gomez | ................ | A61M 5/24 604/416 |
| 3,739,947 A | 6/1973 | Baumann et al. | | |
| 3,802,604 A * | 4/1974 | Morane | ................ | B65D 51/28 222/85 |
| 3,838,689 A * | 10/1974 | Cohen | ................ | A61M 5/31596 604/90 |
| 3,936,264 A * | 2/1976 | Cornett, III | ................ | B65B 3/022 425/525 |
| 4,059,109 A * | 11/1977 | Tischlinger | ................ | A61M 5/284 604/88 |
| 4,861,335 A * | 8/1989 | Reynolds | ................ | B01F 35/7137 604/88 |
| 5,045,063 A * | 9/1991 | Spielberg | ................ | A61M 5/5066 604/218 |
| 5,176,639 A * | 1/1993 | Pozzi | ................ | A61M 5/508 604/110 |
| 5,435,076 A * | 7/1995 | Hjertman | ................ | F26B 5/06 604/416 |
| 5,620,423 A * | 4/1997 | Eykmann | ................ | A61C 5/62 604/218 |
| 6,098,795 A * | 8/2000 | Mollstam | ................ | C12N 1/20 206/219 |
| 6,602,223 B2 * | 8/2003 | Szapiro | ................ | A61M 5/284 604/82 |
| 6,866,653 B2 * | 3/2005 | Bae | ................ | A61M 5/14546 604/191 |
| 7,736,333 B2 * | 6/2010 | Gillespie, III | ................ | A61M 5/2066 604/110 |
| 8,268,263 B2 * | 9/2012 | Campbell | ................ | B01L 3/563 141/330 |
| 8,469,923 B2 * | 6/2013 | Vedrine | ................ | A61M 5/345 604/87 |
| 8,807,177 B2 * | 8/2014 | Strangis | ................ | B63C 9/0005 604/416 |
| 8,833,606 B2 * | 9/2014 | Graham | ................ | B01F 27/0721 206/229 |
| 8,992,469 B2 * | 3/2015 | Bartlett, II | ................ | A61M 5/31596 604/91 |
| 9,623,184 B2 * | 4/2017 | Cronenberg | ................ | A61M 5/31533 |
| 10,486,838 B2 * | 11/2019 | Arnitz | ................ | A61J 1/062 |
| 10,919,187 B2 * | 2/2021 | Faverio | ................ | B29C 39/36 |
| 11,772,060 B2 * | 10/2023 | Dehaudt | ................ | A61K 8/11 206/219 |
| 2004/0122359 A1 * | 6/2004 | Wenz | ................ | B01F 35/713 604/82 |
| 2006/0151629 A1 * | 7/2006 | Vedrine | ................ | B05B 11/0083 239/533.1 |
| 2010/0262074 A1 * | 10/2010 | Seiferlein | ................ | A61J 1/062 53/474 |
| 2011/0224612 A1 * | 9/2011 | Lum | ................ | A61M 5/36 141/2 |
| 2012/0323173 A1 * | 12/2012 | Thorne, Jr. | ................ | A61M 5/31596 604/207 |
| 2012/0325367 A1 * | 12/2012 | Mathys | ................ | A61B 17/8833 141/18 |
| 2013/0223914 A1 * | 8/2013 | Duru | ................ | A45D 34/00 401/172 |
| 2016/0143416 A1 * | 5/2016 | Dourlens | ................ | A45D 40/26 222/386 |

\* cited by examiner

DEVICE FOR PREPARING A COSMETIC COMPOSITION AND ASSOCIATED PROCESS

CROSS REFERENCE TO RELATED APPLICATIONS

This application is a National Phase filing under 35 U.S.C. § 371 of PCT/EP2019/063306 filed on 23 May 2019; which application in turn claims priority to Application No. 18 54311 filed in France on 23 May 2018. The entire contents of each application are hereby incorporated by reference.

The present invention relates to a device for preparing a cosmetic composition comprising:
- a structure defining a housing receiving at least one capsule, the or at least one of the capsules containing at least one constituent of the cosmetic composition,
- an outlet nozzle opening at one end of the housing,
- a piston movable in translation in relation to the structure in the housing, suitable for perforating the or each capsule and conveying contents of each capsule to the outlet nozzle and
- a preform intended to form a receptacle, fluidically connected to the outlet nozzle.

The invention also relates to a process for preparing such a cosmetic composition.

The cosmetic composition prepared by means of the device particularly comprises a cosmetic body surface care, coloring or makeup product.

More generally, a cosmetic composition comprises one or a plurality of cosmetic products, as defined in EC Regulation No. 1223/2009 of the European Parliament and the Council of Nov. 30, 2009, relating to cosmetic products.

The cosmetic compositions are generally commercially available prepared in advance, and packaged in customized individual containers well suited to store distribution.

This type of packaging enables a satisfactory shelf-life and easy handling of the cosmetic composition. Furthermore, it provides the consumer with a guarantee that the packaging contents match the claimed composition, and that they are in compliance with applicable standards.

However, this type of product is not ideal for all clients. Indeed, it does not allow customization of the quantity or precise contents of the cosmetic composition beyond predetermined options. Furthermore, it is not as well-suited to small-scale distribution, for example for retail outlets, that do not always use the section layouts common in stores and superstores.

Devices for filling a container with a cosmetic product extracted from a capsule are known in the prior art, for example in the document FR 3007014. However, these devices do not allow customization of the composition. Furthermore, they do not guarantee that the packaged composition has not been exposed to external contaminants or has not received an additional compound not included in the desired composition. These situations may result in risks of a reduction in product quality, or even health risks.

There is thus a need for a means of preparing and dispensing cosmetics enabling greater customization and being more suitable for retail outlets, while retaining the option of guaranteeing the type and quality of the compositions dispensed.

One aim of the invention is thus that of providing a method for dispensing cosmetics prepared in-situ in a customized manner, and complying with all preexisting quality and traceability requirements.

To achieve this, the invention relates to a device of the type cited above, wherein the preform has an inner surface having a concavity lower than half of a thickness of the preform, intended to be arranged facing the housing and to be deformed by the conveyance of the contents of each capsule, so as to form the receptacle.

Such a device makes it possible to prepare the cosmetic composition and the receptacle effectively, while protecting the composition from any external contamination during preparation, and guaranteeing the integrity and conformity of the composition.

According to particular embodiments, the device according to the invention has one or several of the following characteristics, taken independently or in any technically feasible combination:
- the inner surface is substantially planar and solid.

This alternative embodiment makes it possible to minimize the volume in relation to the preform, particularly for storage purposes.
- the piston is movable in translation along a longitudinal axis of the housing, the inner surface extending perpendicularly to the longitudinal axis.

This alternative embodiment makes it possible to deform the preform symmetrically and homogeneously.
- The device defined above comprises a mold for forming the receptacle, arranged externally with respect to the outlet nozzle.
- The device as defined above comprises means for heating the or each capsule, and optionally the preform and/or mold.

These alternative embodiments make it possible to obtain specific shapes for the receptacle.
- The preform has a substantially planar outer surface, extending substantially parallel with the inner surface.

This alternative embodiment makes it possible to reduce the volume associated with the preform.
- The preform has a substantially cylindrical lateral face having a lateral thread, the outlet nozzle having a threaded internal surface suitable for engaging with the lateral thread of the preform.

This alternative embodiment makes it possible to position the preform on the outlet nozzle simply and quickly.
- The inner surface seals the dispensing nozzle tightly.

This alternative embodiment makes it possible to prevent external air from entering the housing, and prevents any contamination of the cosmetic composition.

The invention also relates to a process for preparing a cosmetic composition, comprising the following steps:
- providing a device as defined above, and at least one capsule, containing at least one constituent of the cosmetic composition, arranged in the housing;
- moving the piston in the housing toward the end, perforating each capsule and conveying the contents of each capsule toward the end, against the inner surface of the preform;
- extruding the contents of each capsule against the preform, via the outlet nozzle, and obtaining the cosmetic composition; and
- simultaneously, deforming the preform (54) to form a receptacle of the cosmetic composition.

According to particular embodiments, the process according to the invention has one or several of the following characteristics, taken independently or in any technically feasible combination:
- The device comprises a mold for forming the receptacle, arranged externally with respect to the outlet nozzle, the deformation of the preform taking place in the mold, an side wall of the receptacle being formed pressing against an inner wall of the mold.

The process as described above comprises a step of heating the preform, and optionally the mold, prior to the piston movement step.

During the piston movement and extrusion steps, the piston, a side wall of each capsule, the outlet nozzle and the preform engage to form a circulation channel fluidically isolated from the outside.

The or one of the capsules is arranged in direct contact with the preform during the provision step.

The piston moves upward through each capsule, the preform being arranged on top of the or each capsule, the receptacle being formed and receiving the cosmetic composition on top of the capsule(s).

Further features and advantages of the invention will emerge after reading the following description given solely as an example with reference to the appended drawings in which.

Figure 1:
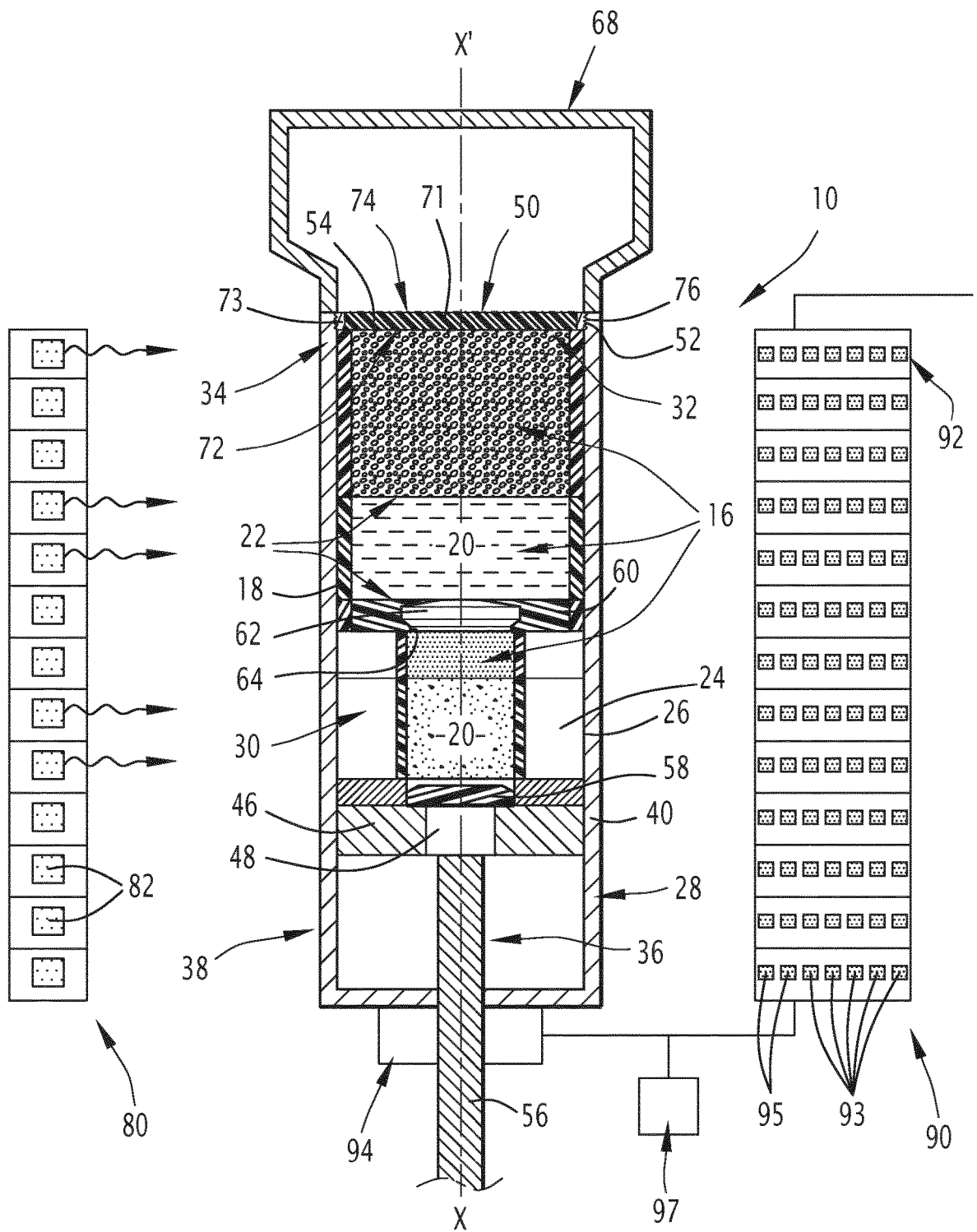
FIGS. 1 to 4 are longitudinal sectional views of a device according to the invention during successive steps of a process for preparing a cosmetic composition.
Figure 2:
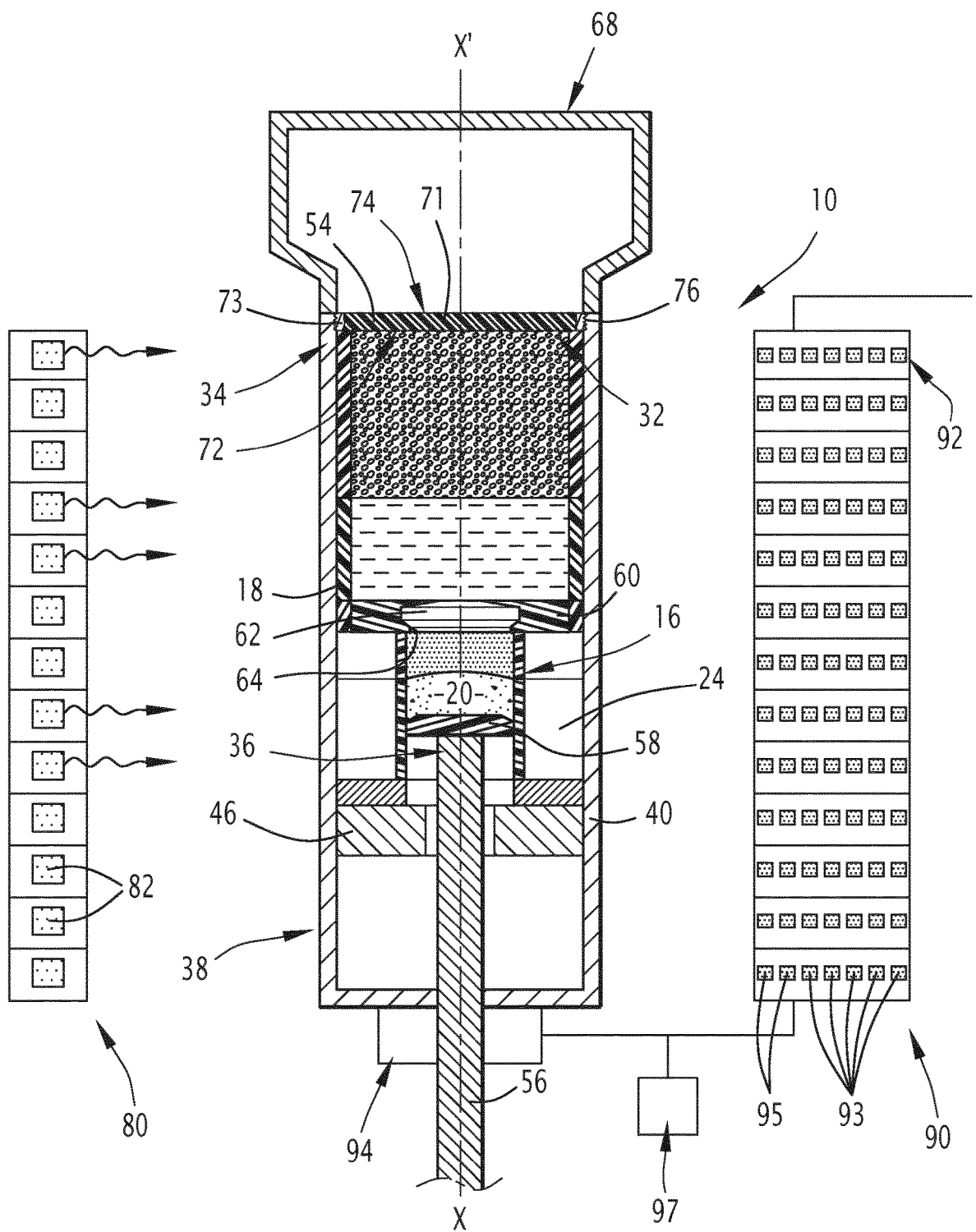

A device 10 for preparing a cosmetic composition 12 is represented in FIGS. 1 to 4. The device 10 is suitable for preparing the cosmetic composition 12, by conveying toward the receptacle 14 and mixing a plurality of constituents of the cosmetic composition 12 contained in at least one capsule 16, and advantageously in a plurality of capsules 16.

The cosmetic composition 12 particularly comprises a cosmetic body surface makeup, care and/or coloring product. The composition 12 is prepared from a plurality of predetermined constituents, in predetermined precise proportions.

The constituents of the cosmetic composition comprise for example one or a plurality of liquids, of varied viscosities, aqueous or organic in nature. The constituents also comprise for example one or a plurality of solids such as powders, particles and/or fibers. Finally, the constituents comprise for example gels, emulsions, creams, foams, or others.

Figure 5:
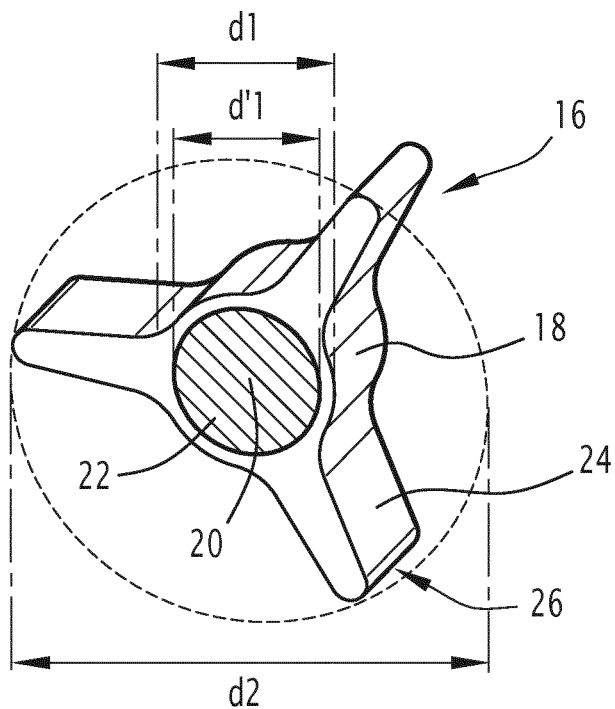
FIGS. 5 to 6 are perspective views of two capsules according to the invention.
Figure 6:
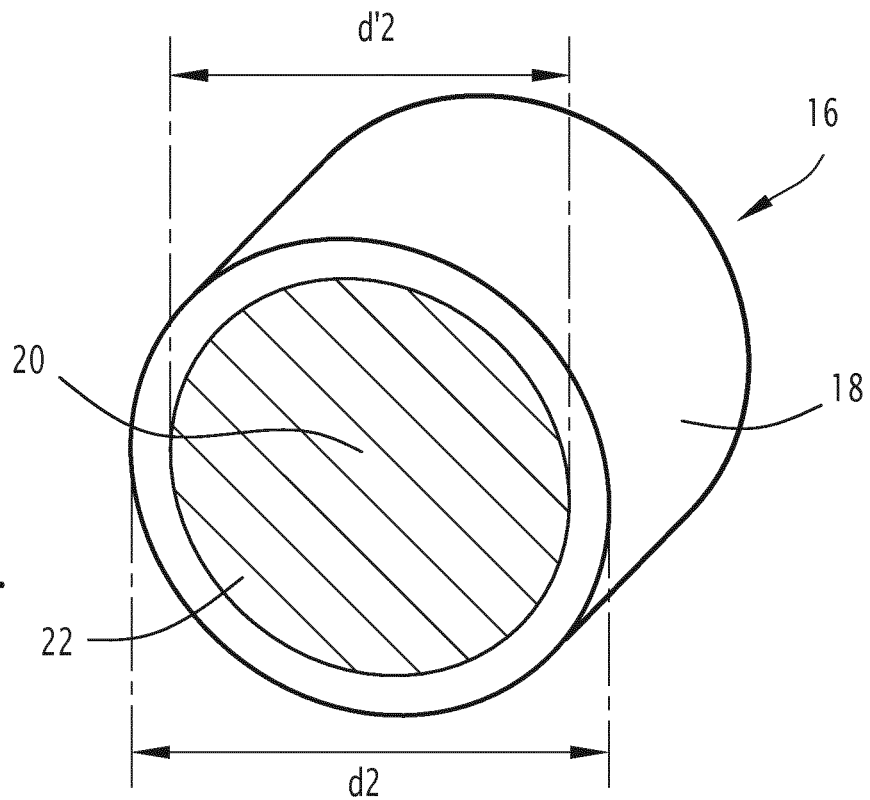

According to a first embodiment represented in the figures, the device 10 receives a plurality of capsules 16. The capsules 16 are represented in FIGS. 5 and 6. Each capsule 16 contains at least one of the constituents of the cosmetic composition 12.

Each capsule 16 comprises a substantially cylindrical side wall 18, defining a substantially inner conduit 20 and two seals 22 closing the inner conduit 20 at two opposite ends.

The term "cylindrical" denotes that the side wall 18 and the inner conduit 20 each have an outer surface in the shape of a cylinder portion, a cylinder being understood to be the geometric shape formed by a generatrix passing through a closed directrix curve inscribed in an orthogonal plane to the generatrix.

According to a first alternative embodiment, the directrix curve is a circle, and the side wall 18 is thus in the shape of a cylinder portion of circular transverse cross-section.

According to further alternative embodiments, the directrix curve is a square, a rectangle, an ellipse, a rhombus, or other shape.

The above definition is applied in the same way hereinafter to any cylindrical object.

The side wall 18 and the inner conduit 20 each have a central axis, which passes through an isobarycenter of the respective directrix curve. The central axes of the side wall 18 and of the inner conduit 20 are particularly coincident.

The side wall 18 is in the form of a solid cylindrical sleeve having a substantially constant thickness on the periphery thereof, and a variable length from one capsule 16 to another. The side wall 18 is for example made of plastic material, and particularly of material transparent to near infrared radiation, such as for example methyl polymethacrylate. Alternatively, the side wall 18 is made of glass.

The plurality of capsules 16 particularly comprises at least one first capsule 16, represented in FIG. 5, and at least one second capsule 16, represented in FIG. 6.

The side wall 18 of each first capsule 16 has the same first outer diameter $d_1$ and the same first inner diameter $d'_1$. The side wall 18 of each second capsule 16 has the same second outer diameter $d_2$, greater than the first outer diameter $d_1$, and the same second inner diameter $d'_2$, greater than the first inner diameter $d'_1$.

In the example shown in the figures, the side wall 18 and the inner conduit 20 are cylindrical with a circular cross-section. In cases where the cross-section of the cylinder is not a circle, the inner $d'_1$, $d'_2$ and outer diameters $d_1$, $d_2$ should be considered as transversal dimensions of the capsules 16, such as for example the side of a square cross-section, or the major axis of an elliptical cross-section.

Each first capsule 16 further comprises fins 24 protruding laterally from the side wall 18, ends 26 of the fins 24 being inscribed in a circle of diameter equal to the second outer diameter $d_2$. The fins 24 are for example of a single piece with the side wall 18.

Each first capsule 16 advantageously comprises at least three fins 24, which helps ensure effective centering of the capsule 16 when it is placed in the device 10.

The seals 22 have a thin disk shape and have a diameter substantially equal to the outer diameter $d_1$, $d_2$ of the side wall 18. The seals 22 are attached to a transversal surface of the side wall 18, for example by heat-sealing.

The seals 22 are made of a stretchable material fragile enough to tear when the seals 22 are stretched beyond a rupture threshold. The seals 22 are for example made of rubber, particularly based on a butadiene-acrylonitrile copolymer (referred to as nitrile rubber), or based on polychloroprene, or based on a latex.

The material forming the seals 22 are advantageously recyclable, particularly by pyrolysis or by grinding and recasting.

Alternatively, the seals 22 are made of a fragile material, the presence whereof in the cosmetic composition causes no discomfort, such as for example from sugar, gelatin, wax, or others.

The inner conduit 20 receives a content of the capsule 16, comprising at least one of the constituents of the cosmetic composition 12.

Each capsule 16 has a specific length, measured between the two ends of the inner conduit 20, and independent of the inner diameter of the capsule 16. The length is determined according to the volume sought for the inner conduit 20, which is dependent on the nature of the contents of the cosmetic composition 12.

Advantageously, the side wall 18 of each capsule 16 has one or a plurality of specific colors, suitable for quickly identifying the contents of the capsule 16 even once the capsule has been placed in the device 10.

Alternatively (not shown), the device 10 receives a single capsule 16 containing all the constituents of the cosmetic composition.

The device 10 comprises a structure 28 defining a housing 30 for receiving the capsules 16, extending along a longitudinal axis X-X'. The device 10 also comprises an outlet nozzle 32 opening at a first end 34 of the housing 30, and a piston 36 mounted at a second end 38 of the housing 30.

The device 10 is particularly positioned vertically, that is to say that the longitudinal axis X-X' extends parallel with gravity, with the outlet nozzle 32 oriented upward, that is to say opening opposite the direction of gravity.

The structure 28 comprises for example a substantially cylindrical casing 40 which defines the housing 30, the outlet nozzle 32 being positioned through the casing 40 and the piston 36 being slidably mounted through the casing 40.

The casing 40 advantageously has openings for accessing the capsules 16. Alternatively, the casing 40 is made of material transparent to near infrared.

Alternatively (not shown), the structure 28 is an open structure comprising a plurality of metal bars extending substantially parallel with the longitudinal axis X-X', defining therebetween the housing 30. The bars are assembled with two end plates, forming the ends of the housing 30, one of the plates comprising the outlet nozzle 32 and the other plate bearing the piston 36. The bars are arranged to serve as lateral support for the ends 26 of the fins 24 of the first capsules 16 and for the side wall 18 of the second capsules 16.

Advantageously, each bar comprises a groove extending facing the housing 30, the grooves being suitable for receiving the ends 26 of the fins 24 of the first capsules 16, so as to prevent the rotation of the first capsules 16 about the longitudinal axis X-X'.

A portion of the structure 28 is movable and/or removable so as to enable the positioning of the capsules 16 in the housing 30.

The housing 30 is a substantially cylindrical internal volume, having a diameter substantially equal to the second outer diameter $d_2$ of the capsules 16. The housing is suitable for receiving the capsules 16 removably, pressing radially on an internal surface of the housing 30.

The definitions of the terms "cylindrical", "axis" and "diameter" given above also apply to the housing 30 and to the piston 36. In particular, the cross-sections of the capsules 16, the housing 30 and the piston 36 are similar.

The capsules 16 received in the housing 30 are aligned along the longitudinal axis X-X', in a coaxial manner. The term coaxial denotes that each of the capsules 16 is arranged with an axis of the inner conduit 20 of the capsule 16 aligned on the longitudinal axis X-X'.

The capsules 16 are arranged in contact with one another, the second capsules 16 being arranged closer to the outlet nozzle 32 situated at the first end 34, and the first capsules 16 being arranged closer to the piston 36 situated at the second end 38.

The side walls 18 of the first capsules 16 are in contact against one another along a parallel direction with the longitudinal axis X-X', so as to form a first circulation conduit 42 having a diameter equal to the first inner diameter $d'_1$.

Similarly, the side walls 18 of the second capsules 16 press against one another along a parallel direction with the longitudinal axis X-X', so as to form a second circulation conduit 44 having a diameter equal to the second inner diameter $d'_2$.

Advantageously, the device 10 also comprises a block 46, slidably mounted in the housing 30, suitable for pressing against the capsule 16 closest to the second end 38 and for fastening capsules 16 pressing against the first end 34 of the housing 30. The block 46 includes a central opening 48 enabling the passage of the piston 36 and access to the inner conduit 20 of the capsules 16.

The block 46 presses on a capsule 16 situated at one end of the stack of capsules 16 to keep the capsules 16 in contact with one another.

The outlet nozzle 32 comprises an opening 50 in the structure 28 opening to the outside of the structure 28 on one side and into the housing 30 on the other, as well as fastening means 52 of a preform 54.

The opening 50 is particularly a circular opening centered on the longitudinal axis X-X'.

The fastening means 52 comprise for example a thread extending onto an internal surface of the opening 50, suitable for engaging with the thread of the preform 54.

Alternatively, the fastening means 52 comprise a clip, bayonet, pin, or other, system.

The piston 36 is mounted on the structure 28, movable in translation relative to the structure 28 along the longitudinal axis X-X' in the housing 30, toward the first end 34.

The piston 36 is also movable through the capsules 16, and suitable for successively stretching the seals 22 of each of the capsules 16 to the rupture threshold thereof, and conveying the contents of the capsule 16 toward the outlet nozzle 32.

The piston 36 comprises a rod 56 extending along the longitudinal axis X-X', as well at least one piston head arranged in the housing 30, suitable for being set in motion by the rod 56.

The piston 36 particularly comprises as many heads, having different outer diameters, as the number of different inner diameters among the capsules 16. The heads are arranged in the housing 30 at a distance from one another along the longitudinal axis X-X', according to an increasing order of diameter toward the first end 34 of the housing 30.

Each head 58, 60 is arranged upstream from the capsule 16 having an inner diameter substantially equal to the outer diameter of the head furthest from the outlet nozzle 32.

In the example shown in FIGS. 1 to 4, the piston 36 comprises a first head 58 and a second head 60, having two different outer diameters, substantially equal respectively to the first inner diameter $d'_1$ and to the second inner diameter $d'_2$ of the capsules 16.

The first head 58 is arranged in contact with the first capsule 16 furthest from the outlet nozzle 32, and the second head 60 is arranged in contact with the second capsule 16 furthest from the outlet nozzle 32.

Each head 58, 60 is arranged to be assembled successively on the rod 56 during the movement of the piston 36 through the housing 30.

In the example shown in the figures, the first head 58 is arranged to be assembled on the rod 56 before passing the piston 36 through the first capsules 16, and the second head 60 is arranged to be assembled on the rod 56 before passing the piston 36 through the second capsules 16.

Each head, with the exception of the head 58 having the smallest outer diameter, defines a through conduit 62, opening onto two opposite faces of the head along the longitudinal axis X-X'.

Advantageously, each conduit 62 is suitable for receiving in a complementary manner the preceding head, particularly in a snap-locking manner. The head received is suitable for sealing the conduit 62 tightly, and preventing the flow of the contents of the capsules 16 through the conduit 62.

In the example shown in the figures, the second head 60 defines the conduit 62, which has an inner diameter substantially equal to the outer diameter of the first head 58.

Figure 3:
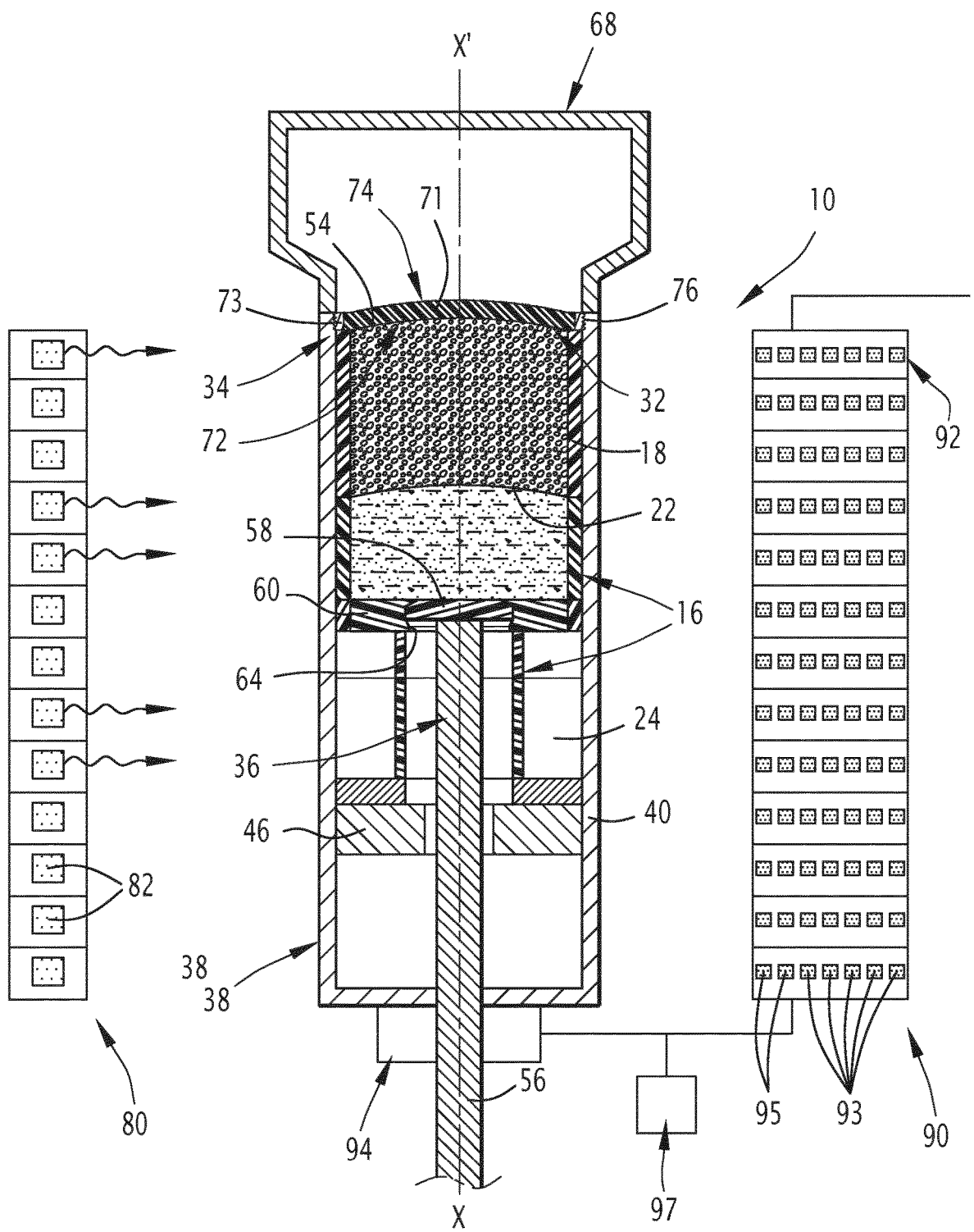
Figure 4:
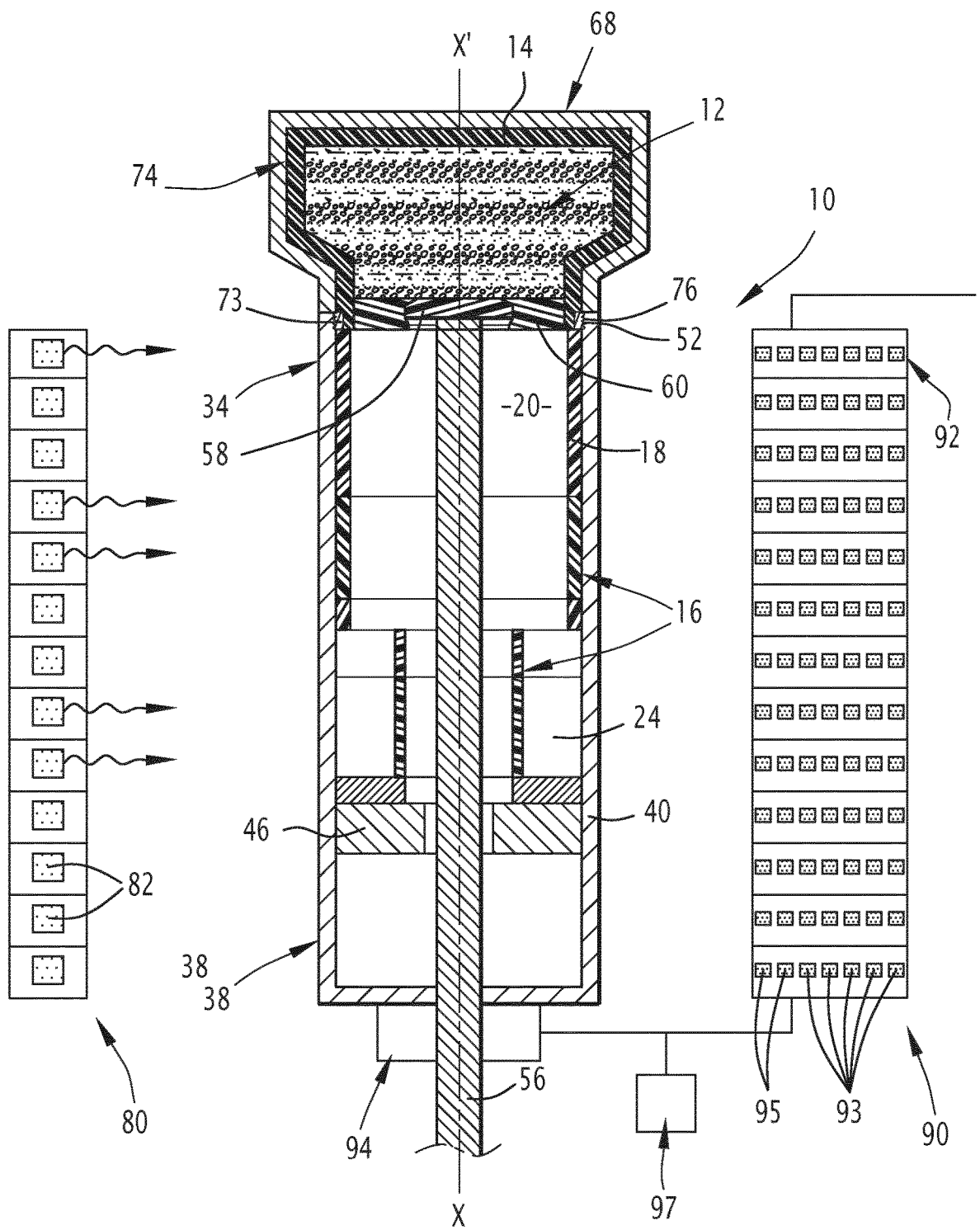

The conduit 62 has a rib 64 extending inside the conduit 62, about an inlet of the conduit 62. The rib 64 reduces the diameter of the conduit at the level of 62 the inlet, so as to fasten the first head 58 received in the conduit 62 by snap-locking, as shown in FIGS. 3 and 4.

Advantageously, at least one of the heads of the piston 36 is suitable for forming a cap 66 of the receptacle 14 connected to the outlet nozzle 32. In particular, all the heads of the piston 36 are suitable for engaging to form the cap 66, as shown in FIG. 4.

The cap 66 is arranged across an inlet of the receptacle 14, after the flow of the cosmetic composition 12 into the receptacle 14. The piston heads 36 are separable from the rod 56 when the receptacle 14 is detached from the outlet nozzle 32 for dispensing the cosmetic composition 12.

The cap 66 is particularly suitable for being perforated after the detachment of the receptacle 14 from the outlet nozzle 32, prior to a first use of the cosmetic composition 12 contained in the receptacle 14.

Advantageously, the cap 66 is suitable for receiving a member for dispensing the cosmetic composition 12, particularly during the perforation of the cap 66. The dispensing member is for example a pump, a dispensing bead, a makeup brush or application brush, a nozzle, a cap, a hinged lid, or other member.

Alternatively, the cap 66 is a rear cap of the receptacle 14, which is intended to be opened on the opposite side of the dispensing cap 66. This case corresponds for example to cosmetic compositions 12 presented in "stick" form, such as for example a lipstick.

As shown in FIGS. 1 to 4, the device 10 comprises a preform 54 received by the outlet nozzle 32, as well as a mold 68 for forming the receptacle 14.

The preform 54 comprises a part 71 made of plastic material, suitable for being heated then deformed irreversibly to form the receptacle 14 receiving the cosmetic composition 12, as well as a retaining ring 73 surrounding the part 71.

The part 71 is particularly suitable for being deformed by the contents of the capsules 16 flowing through the outlet nozzle 32.

The part 71 is particularly rigid at ambient temperature and suitable for softening above a softening temperature, so as to be deformed freely during the flow of the contents from the capsules 16.

Alternatively, the part 71 is suitable for being deformed at ambient temperature, particularly in an elastic, that is to say substantially reversible, manner, during the conveyance of the contents from the capsules 16. The part 71 is for example made of rubber.

The preform 54 has an inner surface 72 of the part 71, facing the housing 30, and an outer surface 74, facing the outside and/or the mold 68. The inner surface 72 is intended to be in contact with the contents of the capsules 16 during the deformation of the preform 54 and to receive the pressure causing the deformation. The outer surface 74 is intended to come into contact with the mold 68 following the deformation of the preform 54.

The inner surface 72 and the outer surface 74 are non-hollow, that is to say the inner surface 72 and the outer surface 74 are flat or slightly concave. The term "slightly concave" denotes that a maximum depth of the concavity is less than half of a transversal thickness of the part 71, measured along the longitudinal axis X-X', and advantageously less than or equal to one quarter of the transversal thickness.

Thus, the part 71 has a shape fully inscribed in a cylinder delimited by two planar surfaces, wherein are inscribed the lateral edges of the inner surface 72 and of the outer surface 74 respectively.

In a preferred embodiment shown in FIGS. 1 to 4, the inner surface 72 is non-concave, substantially planar and solid, and the outer surface 74 is non-convex, particularly substantially planar. The preform 54 is then substantially cylindrical, and has for example a thread 76 on a lateral surface enabling the fastening thereof through the opening 50 of the outlet nozzle 32.

Preferably, the preform 54 is flat. It has a height, measured along the longitudinal axis X-X' thereof, less than the diameter thereof, preferably less than 0.5 times the diameter thereof.

The inner surface 72 of the preform 54 seals, particularly tightly, the opening 50 of the outlet nozzle 32.

Advantageously, the preform 54 is arranged perpendicularly to the longitudinal axis X-X', that is to say with the inner surface 72 extending perpendicularly to the longitudinal axis X-X'. This makes it possible to obtain a homogeneous and symmetrical deformation of the preform 54.

The retaining ring 73 has a lateral thread 76, for fastening the preform 54 to the outlet nozzle 32. The retaining ring 73 is composed of a more heat-resistant material than the part 71, so as not to be degraded when the part 71 is heated and then deformed.

The retaining ring 73 has a smaller inner diameter than the outer diameter $d_2$ of the capsules 16, such that the retaining ring 73, when it is engaged in the thread 54, blocks a translation movement of the capsules 16 along the longitudinal axis X-X' in the housing 30.

Advantageously, the preform 54 and one of the capsules 16 are arranged in contact, so as to ensure the absence of air in the housing 30.

The mold 68 is a surface for forming the preform 54 to obtain the receptacle 14, made for example of metal exhibiting good heat conduction properties.

The mold 68 is for example arranged to enable the removal of the receptacle 14 containing the cosmetic composition 12, once the preform 54 has been formed, and to be put back in place for another use.

Alternatively, the mold 68 is single-use and is part of the receptacle 14 containing the cosmetic composition 12.

Advantageously, the device 10 also comprises a device 80 for heating the capsules 16, arranged in the vicinity of the housing 30, and a protective casing (not shown) arranged externally with respect to the heating device 80 and the housing 30. The heating device 80 is suitable for heating each of the capsules 16 inserted in the housing 30, independently, so as to bring the contents of the capsule 16 to a desired temperature.

Advantageously, the heating device 80 is also suitable for heating the mold 68 and/or the preform 54.

The heating device 80 particularly comprises a plurality of sources 82 of infrared radiation, arranged to emit each of the infrared rays to one of the capsules 16, with an individually modulated power.

The sources 82 are arranged to emit through the access openings to the capsules 16 of the casing 40, or between the bars of the structure 28 depending on the case.

The rays have frequencies in the near infrared range, for example between 800 nm and 3 μm.

The rays are suitable for passing through the side wall 18 of the capsules, which is made of a material transparent to near infrared rays, and for directly heating the contents of the capsules 16 individually.

The power emitted by each source 82 is determined so as to bring the contents of the capsule 16 to which the source 82 emits to a predetermined desired temperature.

Advantageously, the device 10 further comprises a checking system 90 of the capsules 16 fitted in the housing 30. The checking system 90 is suitable for determining whether the capsules 16 fitted in the housing 30 are suitable for contributing to the preparation of the cosmetic composition 12, that is to say whether the capsules 16 correspond to a formula of the cosmetic composition 12 to be prepared, and/or whether each of the capsules 16 is suitable for use for preparing the cosmetic composition 12.

The checking system 90 comprises for example a plurality of spectrometry cells 92, aligned parallel with the longitudinal axis X-X' and arranged facing the capsules 16, intended to analyze the contents of each capsule 16 by spectrometry, using frequencies belonging to a spectrum comprising the infrared, visible, and/or near ultraviolet range.

Each cell 92 comprises for example at least one diode 93 suitable for emitting rays toward the capsules 16, and at least one optical sensor 95 suitable for collecting the rays having interacted with the capsules 16 and for measuring a spectrum in a frequency band.

The checking system 90 further comprises a processing module 97, particularly comprising a processor and a memory.

The processing module 97 is suitable for controlling each cell 92, analyzing the measurement results of the sensors 95 and reconstructing the signature of the capsule 16.

Each diode 93 is suitable for emitting rays having a frequency included in a specific band of the diode 93. For example, each cell 92 comprises a red diode 93, a green diode 93, a blue diode 93, and two diodes 93 emitting in the ultraviolet range.

The red, green and blue diodes 93 are suitable for emitting rays having a frequency included in the band between 600 nm and 700 nm, between 500 nm and 550 nm and between 470 nm and 490 nm, respectively.

The diodes 93 emitting in the ultraviolet range are suitable for emitting rays having a frequency included in the ultraviolet spectrum, that is to say for example between 100 nm and 400 nm. Advantageously, the two UV diodes emit rays wherein the frequencies are in two distinct bands of the ultraviolet spectrum.

Each sensor 95 is suitable for measuring a spectrum in a frequency band, that is to say a profile of the intensities of the rays collected according to the frequency thereof.

Each cell 92 comprises for example a measurement sensor 85 in the visible spectrum, such as a phototransistor, and a measurement sensor 95 in the ultraviolet spectrum.

The cell 92 is thus suitable for measuring a signature of the capsule 16 facing the cell 92, under the control of the processing module 97.

The signature of the capsule 16 is a frequency spectrum of the rays collected by the sensors 95, and is dependent on the frequencies of rays absorbed and transmitted by the capsule 16, that is to say by the side wall 18 and by the contents.

The signature of each capsule 16 is measured by emitting toward the capsule 16 rays having predetermined respective intensities and frequencies, by means of the diodes 93, by measuring by means of the sensors 95 the spectra of the rays collected by the capsules 16, and reconstructing the signature of the capsule 16 by means of the processing module 97.

The signature of each capsule 16 is characteristic of the contents of the capsule 16 and of the side wall 18, and makes it possible to identify the capsule 16 from a database stored in the memory, and containing the signature templates of the different capsules 16 suitable for use with the device 10.

The processing module 97 is suitable for comparing the signature of each capsule 16 to templates stored in the database to determine the nature and contents of the capsules 16 placed in the housing 30. The processing module 97 is also suitable for comparing the capsules 16 in the housing 30 to cosmetic composition formulas stored in the database and determining whether there is a match. Finally, the processing module 97 is suitable for allowing the preparation of the cosmetic composition 12 if there is a match, and for preventing it otherwise.

For example, the processing module 97 is connected to an activator 94 of the piston 36, so as to allow the movement of the piston 30 only if it determines a match between the capsules 16 placed in the housing 30 and a formula stored in the memory. In particular, the processing module 97 is suitable for allowing an electrical contact between an external energy source and the actuator 94 only if the capsules 16 are determined to be suitable for contributing to the formation of the cosmetic composition 12.

Advantageously, the checking system 90 is also suitable for determining the lengths of the capsules 16 arranged in the housing 30. Indeed, if a plurality of adjacent cells 92 measure an identical signature, the processing module 97 determines that the same capsule 16 extends facing the cells 92 in question and can thus determine the length of the capsule 16 among the possible dimensions.

Advantageously, the checking system 90 is further suitable for determining whether one of the capsules 16 arranged in the housing 30 is unfit for use.

For example, the checking system 90 is suitable for measuring the presence of a marker previously placed on the side wall 18 of the capsule 16, and enabling the activation of the piston 36 only if each of the capsules 16 has the marker.

The marker is for example a substance placed on the side wall 18 and having a characteristic signature in the frequency bands of the diodes and the sensors. The marker is degraded after a certain time or above a certain temperature and no longer has the same characteristic signature. The marker is for example vitamin C, or avobenzone.

This alternative embodiment makes it possible to check the validity of the capsules 16, and prevent the filling and reuse thereof, since the marker is degraded after the first use of the capsule 16.

According to an alternative embodiment not shown, the checking system 90 comprises at least one infrared diode 93 and at least one infrared sensor 95 arranged on an opposite side of the housing 30, to measure the spectrum of the infrared rays traversing the capsule 16.

According to an alternative embodiment not shown, the checking system 90 comprises a digital camera intended to analyze the external appearance of the capsules 16, and particularly that of the side wall 18, so as to determine the nature of the contents of each of the capsules 16, by means of an image analysis performed by the processing module 97, substituting the cells 92.

According to an alternative embodiment not shown, the first capsules 16 do not include fins 24. The device 10 includes in this case at least one independent removable insert for reducing the diameter of the housing 30. The insert is for example in the form of a substantially cylindrical sleeve and has an outer diameter substantially equal to the second outer diameter $d_2$. The insert defines a substantially cylindrical secondary housing for receiving the first capsules 16 having an inner diameter substantially equal to the first outer diameter $d_1$.

The secondary housing opens at two opposite ends of the insert, so as to enable the circulation of the first head 28 and of the contents of the first capsules 16 toward the outlet nozzle 34.

Alternatively, the insert is composed of a plurality of bars substantially parallel with one another, assembled with two end structures by the respective ends thereof, and defining the secondary housing therebetween.

Advantageously, the insert has a sufficient length to receive a plurality of first capsules 16 positioned end to end in the secondary housing.

Advantageously, the insert comprises two parts, for example connected by a hinge, so as to facilitate the positioning of the capsules 16.

A process for preparing the cosmetic composition 12 using the preparation device 10 will now be described.

During a preliminary step, a set of capsules 16, each containing constituents of the composition 12, is selected according to the nature of the composition 12 sought.

During a first step, the capsules 16 are arranged in the housing 30. The capsules 16 are arranged aligned along the longitudinal axial X-X', in a coaxial manner, according to an increasing order of diameter toward the outlet nozzle 32.

Piston heads corresponding to the different diameters of the capsules 16 are also inserted into the housing 30, arranged between the groups of capsules 16 having the same inner diameter.

For example, the set of capsules 16 comprises first capsules 16 and second capsules 16 as described above. A first head 58 having an outer diameter equal to the first inner diameter $d'_1$ is positioned upstream from the first capsules 16, relative to the direction of travel of the piston 36. A second head 60 having an outer diameter equal to the second inner diameter $d'_2$ is positioned before the second capsules 16, relative to the direct of travel of the piston 36.

The block 46 is then moved in the housing 30, along the longitudinal axis X-X', until contact of the first capsules 16, so as to position the capsules 16 pressing against one another and against the outlet nozzle 32.

The side walls 18 of the first capsules 16 then form the first circulation conduit and the side walls of the second capsules 16 then form the second circulation conduit.

The process then comprises a step of positioning a preform 54, connected to the outlet nozzle 32. The preform 54 is fluidically connected, tightly, to the opening 50 of the outlet nozzle 32, so as to receive the contents of capsules 16 flowing through the outlet nozzle 32.

The preform 54 is fastened by fastening means 52 to the outlet nozzle 32.

The preform 54 is particularly positioned without introducing into the housing air from outside the device 10.

The capsule 16 closest to the first end 34 is particularly arranged in contact with the preform 54.

The process comprises a step of heating the preform 54, and optionally the mold 68, so as to allow the deformation of the preform 54. The preform 54 is for example heated up to a softening temperature of the part 71.

The process then optionally comprises a step of heating each capsule 16 individually by means of the device for heating the capsules 16, during which the contents of each capsule 16 are heated to a predetermined temperature, for example to fluidify same and facilitate the flow and miscibility thereof.

The process advantageously comprises a step of determining the property of capsules 16 of taking part in the preparation of the cosmetic composition 12. The checking device 90 measures the signature of each of the capsules 16 and determines the nature and contents of each of the capsules 16, as well as the presence of the non-degraded marker on the side wall 18 of the capsules 16.

If the capsules 16 arranged in the housing 30 match a valid formula of the cosmetic composition 12 saved in the memory, and if the non-degraded marker is present on the capsules 16, the checking device 90 allows the movement of the piston 36. Otherwise, the checking device 90 signals an error.

The process then comprises a step of moving the piston 36 along the longitudinal axis X-X', toward the outlet nozzle 32, through the housing 30 and through the capsules 16.

The step of moving the piston 36 comprises a first substep during which the rods 56 moves in contact with the first head 58, followed by successive substeps of moving the piston 36 through each first capsule 16, stretching the seals 22 of each capsule 16 to the rupture threshold thereof, and conveying the contents of the first capsules 16 toward the first end 34. The contents of the first capsules 16 flow particularly through the conduit 62 defined by the second head 60 and are mixed in the conduit 62.

The seals 22 are stretched successively about the piston 36 and line the walls of the first circulation conduit. Each seal 22 tears once the rupture threshold has been reached, so as to enable the flow of the contents from the capsules 16. The seal 22 tears cleanly, without forming debris in the first circulation conduit, and retracts upstream from the piston 36.

The step of moving the piston 36 then comprises a substep of moving the piston 36 in contact with the second head 60, pressing the piston 36 on the second head 60, and assembling the second head 60 on the first head 58 particularly by snap-locking.

The step of moving the piston 36 then comprises substeps of moving the piston 36 through each second capsule 16 and stretching each seal 22 of the second capsules 16, and conveying the contents of the capsules 16 toward the first end 34.

The process then comprises a step of extruding the contents of the capsules 16 through the opening 50 of the outlet nozzle 32, against the preform 54.

Advantageously, during the movement of the piston 36 and the extrusion of the contents of the capsules 16, the piston 36, the side walls 18 of the capsules 16, the outlet nozzle 32 and the preform 54 engage to form a circulation channel fluidically isolated from the outside. The side walls 18 of the capsules 16 and the head(s) 58, 60 are in tight contact, making it possible to prevent an entry of air from outside the device 10, which could contaminate the cosmetic composition 12.

The process comprises a step of deforming the preform 54 so as to form the receptacle 14. The contents of the capsules 16 flow against the inner surface 72 of the preform 54 and exert thereon a pressure which deforms the preform 54. The preform 54 is deformed irreversibly and becomes the receptacle 14 receiving the cosmetic composition 12, particularly in a mold 68.

The process finally comprises a step of engaging at least one of the heads of the piston 36 in the receptacle 14, so as to form a cap of the receptacle 14. The cap is particularly snap-locked in the opening of the receptacle 14.

For example, the first head 58 and the second head 60 are assembled with one another and form a cap of the receptacle 14.

The process comprises steps of detaching the receptacle 14 from the outlet nozzle 32 and removing the perforated capsules 16 from the housing 30.

Optionally, the process further comprises a step of perforating the cap and positioning a member for dispensing the cosmetic composition 12 on the cap.

Advantageously, the process comprises steps of positioning a new preform 54, as well as introducing in the housing 30, removably, a new plurality of capsules 16, as described above, each capsule 16 containing at least constituent of a new cosmetic composition 12.

The device 10 makes it possible to prepare the cosmetic composition 12 and the receptacle 14 effectively, while protecting the composition 12 from any external contamination during preparation, and guaranteeing the integrity and conformity of the composition 12.

The flat shape of the preform 54 makes it possible to minimize the volume thereof, particularly for storage purposes.

Furthermore, the flat preform 54 arranged in contact with the capsules 16 makes it possible to prevent external air from entering the housing 30, and prevents any contamination of the cosmetic composition 12.

The system 90 for checking the capsules 16 makes it possible to ensure that the contents of the capsules 16 are indeed suitable for forming the cosmetic composition 12, and that the capsules 16 arranged in the housing indeed match a valid cosmetic composition 12 formula.

In a variant (not shown), the side walls 18 of at least some of the capsules 16 present reliefs on the external cylindrical surface thereof, like ribs and/or grooves. These reliefs are obtained through molding and/or machining of the side walls 18, and allows for easier identification of the capsule 18 and its content by an operator.

In a variant (not shown), the seals 22 are integral with the side walls 18, and thin enough to be deformed and broken by the piston 36 moving through the housing 30.

EXAMPLES

In a first example, the cosmetic composition 12 prepared is a shampoo.

The capsules 16 inserted into the housing 30 comprise, in the order from the furthest to the closest to the outlet nozzle 31:
- a first capsule containing a first surfactant, such as for example polysorbate, of outer diameter equal to 1.2 cm and length equal to 1 cm,
- two first capsules containing a second surfactant, such as for example sodium lauryl ether sulfate, of outer diameter equal to 1.2 cm and length equal to 3 cm,
- two first capsules containing a polymer, for example a copolymer of acrylamide and quaternary ammonium salts, known under the name polyquaternium-7, of diameter equal to 1.2 cm and length equal to 3 cm,
- four first capsules containing a third surfactant, such as cocamidopropyl betaine, of outer diameter equal to 1.2 cm and length equal to 3 cm,
- a first capsule containing a fourth surfactant, such as for example cocamide monoethanolamine, of diameter equal to 1.2 cm and length equal to 1 cm,
- two second capsules containing a solvent, such as for example water, of diameter equal to 3.6 cm and length equal to 3 cm.

The capsules 16 are traversed by the piston 36 in the order indicated and the contents thereof conveyed to a receptacle 14 attached to the outlet nozzle 31, which prepares the cosmetic composition 12.

In a second example, the cosmetic composition 12 prepared is a lip balm.

The capsules 16 inserted into the housing 30 comprise, in the order from the furthest to the closest to the outlet nozzle 31:
- a first capsule containing a first solvent, such as for example 1,2-octanediol, also known under the name caprylyl glycol, of outer diameter equal to 1.2 cm and length equal to 1 cm,
- a first capsule containing a first fatty substance, such as for example petroleum jelly, of outer diameter equal to 1.2 cm and length equal to 3 cm,
- a first capsule containing a second solvent, for example glycerin, of diameter equal to 1.2 cm and length equal to 3 cm,
- four first capsules containing a first surfactant, such as isostearyl alcohol, of outer diameter equal to 1.2 cm and length equal to 1 cm,
- five first capsules containing a second fatty substance, such as for example caprylic/capric triglyceride, of diameter equal to 1.2 cm and length equal to 1 cm,
- two first capsules containing a second surfactant, for example sodium stearate, of diameter equal to 1.2 cm and length equal to 3 cm,
- three first capsules containing a first solvent, for example tripropylene glycol, of diameter equal to 1.2 cm and length equal to 3 cm,
- a second capsule containing a silicone oil, of diameter equal to 3.6 cm and length equal to 1 cm,
- a second capsule containing a second solvent, such as for example water, of diameter equal to 3.6 cm and length equal to 3 cm.

The capsules 16 are traversed by the piston 36 in the order indicated and the contents thereof conveyed to a receptacle 14 attached to the outlet nozzle 31, which prepares the cosmetic composition 12.

The invention claimed is:

1. A device for preparing a cosmetic composition, the device comprising:
    a structure defining a housing receiving at least one capsule, the or at least one of the capsules containing at least one constituent of the cosmetic composition,
    an outlet nozzle opening at one end of the housing,
    a piston movable in translation in relation to the structure in the housing, suitable for perforating the or each capsule and conveying contents of each capsule to the outlet nozzle, and
    a preform intended to form a receptacle, fluidically connected to the outlet nozzle,
    characterized in that the preform has an inner surface having a concavity lower than half of a thickness of the preform, intended to be arranged facing the housing and to be deformed by the conveyance of the contents of each capsule, so as to form the receptacle, and wherein the device further comprises a mold for forming the receptacle, arranged externally with respect to the outlet nozzle.

2. The device according to claim 1, wherein the inner surface is substantially planar and solid.

3. The device according to claim 2, wherein the piston is movable in translation along a longitudinal axis (X-X') of the housing, the inner surface extending perpendicularly to the longitudinal axis (X-X').

4. The device according to claim 2, comprising a mold for forming the receptacle, arranged externally with respect to the outlet nozzle.

5. The device according to claim 2, comprising means for heating the or each capsule and optionally the preform and/or mold.

6. The device according to claim 1, wherein the piston is movable in translation along a longitudinal axis (X-X') of the housing, the inner surface extending perpendicularly to the longitudinal axis (X-X').

7. The device according to claim 6, comprising a mold for forming the receptacle, arranged externally with respect to the outlet nozzle.

8. The device according to claim 6, comprising means for heating the or each capsule and optionally the preform and/or mold.

9. The device according to claim 1, wherein the preform has a substantially planar outer surface, extending substantially parallel with the inner surface.

10. The device according to claim 1 wherein the inner surface-seals the dispensing nozzle tightly.

11. A device for preparing a cosmetic composition, the device comprising:
a structure defining a housing receiving at least one capsule, the or at least one of the capsules containing at least one constituent of the cosmetic composition,
an outlet nozzle opening at one end of the housing,
a piston movable in translation in relation to the structure in the housing, suitable for perforating the or each capsule and conveying contents of each capsule to the outlet nozzle, and
a preform intended to form a receptacle, fluidically connected to the outlet nozzle,
wherein the preform has an inner surface having a concavity lower than half of a thickness of the preform, intended to be arranged facing the housing and to be deformed by the conveyance of the contents of each capsule, so as to form the receptacle and wherein the device further comprises means for heating the or each capsule, and optionally the preform and/or mold.

12. A device for preparing a cosmetic composition, the device comprising:
a structure defining a housing receiving at least one capsule, the or at least one of the capsules containing at least one constituent of the cosmetic composition,
an outlet nozzle opening at one end of the housing,
a piston movable in translation in relation to the structure in the housing, suitable for perforating the or each capsule and conveying contents of each capsule to the outlet nozzle, and
a preform intended to form a receptacle, fluidically connected to the outlet nozzle,
wherein the preform has an inner surface having a concavity lower than half of a thickness of the preform, intended to be arranged facing the housing and to be deformed by the conveyance of the contents of each capsule, so as to form the receptacle, wherein the preform has a substantially cylindrical lateral face having a lateral thread, the outlet nozzle having a threaded internal surface suitable for engaging with the lateral thread of the preform.

13. A process for preparing a cosmetic composition, comprising the following steps:
providing a device according to claim 1 and at least one capsule, containing at least one constituent of the cosmetic composition, arranged in the housing;
moving the piston in the housing toward the end, perforating each capsule and conveying the contents of each capsule toward the end, against the inner surface of the preform;
extruding the contents of each capsule against the preform, via the outlet nozzle, and obtaining the cosmetic composition; and
simultaneously, deforming the preform to form a receptacle of the cosmetic composition.

14. The process according to claim 13, wherein the device comprises a mold for forming the receptacle, arranged externally with respect to the outlet nozzle, the deformation of the preform taking place in the mold, an side wall of the receptacle being formed pressing against an inner wall of the mold.

15. The process according to claim 13, comprising a step of heating the preform, and optionally the mold, prior to the piston movement step.

16. The process according to claim 13, wherein during the piston movement and extrusion steps, the piston, a side wall of each capsule, the outlet nozzle and the preform engage to form a circulation channel fluidically isolated from the outside.

17. The process according to claim 13, wherein the or one of the capsules is arranged in direct contact with the preform during the provision step.

18. The process according to claim 13, wherein the piston moves upward through each capsule, the preform being arranged on top of the or each capsule, the receptacle being formed and receiving the cosmetic composition on top of the capsule(s).

* * * * *